United States Patent [19]

Pelletier et al.

[11] Patent Number: 4,614,115

[45] Date of Patent: Sep. 30, 1986

[54] ULTRASONIC PROCESS AND APPARATUS FOR MONITORING AND MEASURING THE EVOLUTION WITH TIME OF PHYSICO-CHEMICAL, BIOLOGICAL OR BACTERIOLOGICAL PHENOMENA

[75] Inventors: Jean L. Pelletier, Ploubazlanec; Michel Moreau, Yerres; Michel Bocquet, Issy.Les.Moulineaux, all of France

[73] Assignee: Societe d'Etudes et de Recherches de l'Ecole Nationale Superieure d'Arts et Metiers Seram, France

[21] Appl. No.: 691,563

[22] PCT Filed: Apr. 9, 1984

[86] PCT No.: PCT/FR84/00097

§ 371 Date: Dec. 7, 1984

§ 102(e) Date: Dec. 7, 1984

[87] PCT Pub. No.: WO84/04167

PCT Pub. Date: Oct. 25, 1984

[30] Foreign Application Priority Data

Apr. 12, 1983 [FR] France .................. 83 05910

[51] Int. Cl.⁴ ............................................. G01N 29/00
[52] U.S. Cl. ................................. 73/599; 73/32 A; 73/290 V; 73/589; 73/629; 73/644

[58] Field of Search ............... 73/644, 589, 599, 629, 73/627, 32 A, 290 V

[56] References Cited

U.S. PATENT DOCUMENTS

| | | | |
|---|---|---|---|
| 4,320,659 | 3/1982 | Lynnworth et al. | 73/589 |
| 4,325,255 | 4/1982 | Howard et al. | 73/589 |
| 4,414,849 | 11/1983 | Brown et al. | 73/599 |

FOREIGN PATENT DOCUMENTS

2060883  5/1981  United Kingdom .

*Primary Examiner*—Howard A. Birmiel
*Attorney, Agent, or Firm*—Gerald J. Ferguson, Jr.; James E. Bryan; Michael P. Hoffman

[57] ABSTRACT

Ultrasonic process and apparatus for monitoring and measuring the evolution with time of physico-chemical and biological phenomena. There is plunged into the medium or media (4) to be monitored a bar (3) into which ultrasound (2) is injected in order to collect secondary echoes (F2, F3) due to numerous reflections from the lateral surface of the bar (3) brought into contact with the medium (4), one of the secondary echoes (F2) is selected and the evolution with time of the amplitude of this echo is recorded, this representing the evolution of the medium being monitored, in particular the setting of concrete or the polymerization of a resin.

12 Claims, 17 Drawing Figures

ULTRASONIC PROCESS AND APPARATUS FOR MONITORING AND MEASURING THE EVOLUTION WITH TIME OF PHYSICO-CHEMICAL, BIOLOGICAL OR BACTERIOLOGICAL PHENOMENA

The object of the invention is an ultrasonic process and apparatus for monitoring and measuring the evolution with time of certain physical and/or chemical characteristics within a changing medium or between two media.

The invention is of utility in the cases cited below by way of non-limiting examples:

measuring the setting time of a hydraulic binder, evaluating the time for a paint to dry or an adhesive to harden, studying changes of state, from the solid state to the liquid state or vice versa, physico-chemical modification of a contact (oxidation-work hardening), crystallization of a substance in solution or sedimentation of a substance in suspension, polymerization of a plastics material, evaluation of blood coagulation and/or sedimentation time, studying the curdling of milk.

It has already been proposed to use an ultrasonic apparatus to detect certain physical or chemical phenomena. In this respect, the state of the art is illustrated by British Pat. No. 2 060 883 which describes a frost detector. According to this patent voltage pulses at an ultrasonic frequency are applied to a winding which surrounds a bar connected to a rod laid in a trench dug into the surface of a road. The bar is of a material which exhibits a magnetostrictive effect under the influence of the magnetic field created in the winding. This results in vibrations at ultrasonic frequencies which are transmitted into the rod and which are reflected at its walls. The way in which they are reflected differs according to whether the rod is in contact with water or with ice. On the other hand, by virtue of magnetostriction the bar induces voltage pulses in the winding because of the reflected vibrations. These pulses are collected and from them it is possible to deduce whether the rod is surrounded with water or ice. The use of magnetostriction is essential in this patent.

In U.S. Pat. No. 4,320,659 there is described an apparatus for measuring the accoustic impedance of a medium or for detecting the level of a liquid. To this end, a vertically polarized transverse ultrasonic wave is fed into a bar with a particular angle of incidence from a lateral surface or an end surface which is inclined so that this wave is propagated in zig-zag fashion by successive reflections; the wave collected at a remote point is different by virtue of the coupling which is produced between the bar and the medium in which it is immersed. In a variation, the polarized transverse wave is fed into the bar through an end face but the ultrasonic beam is subject to reflections which are propagated parallel to the axis of the bar; moreover, the bar has a lateral surface featuring longitudinally spaced notches which serve as reflection surfaces. The reflections collected differ according to the nature or the level of the medium with which the bar is in contact. The use of polarized transverse waves is essential in this patent.

Also known is the use of ultrasound for measuring thicknesses or lengths of parts or for locating the evaluating defects (scale, cracks, splits). The reading is made immediately after the echo obtained as a result of reflection of the waves emitted in the longitudinal direction. The secondary echoes have something of a nuisance value in that the reading is taken only on the main echoes of the longitudinal waves emitted parallel to the axis.

In all these examples, ultrasound is utilized with a limited objective (detection of frost, detection of defects, measurement of distance, detection of level, etc) under specific operating conditions (detection of direct echoes only, deliberate creation of vertically or horizontally polarized waves, use of waves directed in zig-zag fashion, use of reflecting surfaces at predetermined locations, etc).

The invention is distinguished from these known uses limited to specific cases in the sense that it provides a general purpose process for monitoring and measuring the evolution in time of sundry phenomena within a medium or between two media, in accordance with which there is immersed in this medium or these media at least part of the length of the lateral surface of an elongate bar into which ultrasonic waves are injected via an injection surface so as to favor within the bar the creation of beams of secondary waves reflected from the entirety of said lateral surface, these secondary echoes are collected, at least one of them is isolated and the evolution in time of its amplitude is recorded.

An end surface of the bar perpendicular to its longitudinal dimension is preferably used as the injection surface.

The secondary echoes are advantageously collected at the injection end surface.

Use is preferably made of waves at a frequency between 1 MHz and 20 MHz and bars having a thickness of between 8 mm and 30 mm in the transverse direction.

Within the principle of the invention, an optimum result is obtained when the frequency is related to the size (preferably the diameter) of the bar employed. For example, with frequencies of 2, 5, 10, 15 and 20 MHz it is advantageous to utilize cylindrical bars having diameters of 30, 20, 15, 10 and 8 mm, respectively.

These values of the frequencies and the diameters are not critical, however, but they constitute values which it is preferable to approximate in order to obtain the best results.

Further, the secondary echoes of the first through fourth orders are preferably selected for measuring the evolution of the medium under study.

The invention also concerns an apparatus comprising a probe constituted by an ultrasonic transmitter-receiver member and by an elongate bar coupled via one surface to this member and designed to be immersed in a changeable or reactive medium, and a measuring device connected to the probe to measure the characteristics of the ultrasonic waves emitted and of the waves reflected by the bar when this is in contact through its lateral surface with a changeable or reactive medium, in which apparatus, in accordance with the invention, this elongate bar is coupled to the transmitter-receiver member through an end surface perpendicular to its longitudinal dimension and its lateral surface is smooth, so that secondary ultrasonic waves are reflected in beams by the entirety of this lateral surface, the measuring device being provided with electronic means capable of selecting at least one of the secondary echoes reflected by the lateral wall and of measuring and recording the evolution with time of the amplitude of this or these selected secndary echo(es).

The elongate bar preferably has a length at least three times its diameter.

The bar is preferably of a material which is a good conductor of ultrasound, which is capable of taking a high polish on its lateral surface, which has a ratio of the propagation speed of the longitudinal to transverse waves which is between 1.57 and 1.70 and preferably approximately 1.65, and which has a low impedance.

When account is taken also of the fact that the bar is intended to be immersed in highly diverse media, sometimes for extended periods, it is preferable to employ a material which is resistant to corrosion.

In accordance with the invention, the bar employed is preferably a drawn glass rod.

The bar is advantageously joined to an ultrasonic generator in a detachable manner as by demounting or breaking off.

A description will now be given of several examples of embodiments of the invention, without limiting intention and without excluding any variant. Reference should be had to the appended drawings in which:

FIG. 3 is a schematic drawing showing the formation of a secondary echo in the bar of the apparatus of FIG. 1, FIGS. 4a and 4b schematically represent beams of secondary echoes of the ultrasonic waves within a bar first immersed in air and then immersed in a different medium, FIGS. 4a' and 4b' are A-scope representations corresponding to FIGS. 4a and 4b, FIGS. 5 through 11 are graphs showing the evolution of various media recorded with the apparatus of FIG. 1.

Figure 1:
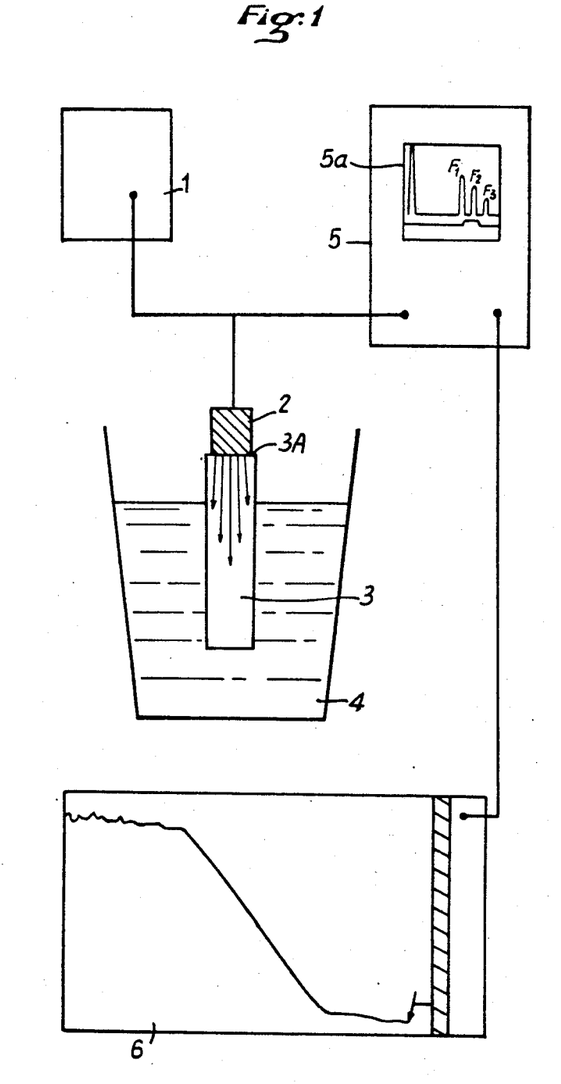
FIG. 1 is a schematic representation of an apparatus in accordance with the invention for utilizing the process of the invention.

FIG. 1 shows an apparatus in accordance with the invention comprising a generator 1 producing pulses at a frequency of 15 MHz connected to a probe consisting of a ceramic transmitter-receiver head 2 and an elongate bar 3 which is immersed in a medium 4 to be studied. This probe will be described in detail hereinafter. The generator 1 applies electrical pulses to the ceramic, generally referred to as a transducer, which emits longitudinal ultrasonic waves which propagate in the bar 3 from one of its end faces 3a. The cross-section of the transducer is similar to that of the bar 3 which is subject to intense ultrasonic activity as a result of echoes caused by the reflection of the waves on the one hand from the end face opposite the emitting end face and on the other hand and above all from the entirety of the lateral surface of the bar. The generator 1 and the transmitter-receiver ceramic 2 are connected to an oscilloscope-type known device 5a with echo selector itself connected to a recording device 6, an X-Y plotter for example, capable of recording as a function of time the variation in the height of a selected secondary echo originating from the secondary waves (S in FIG. 3).

Figure 2:
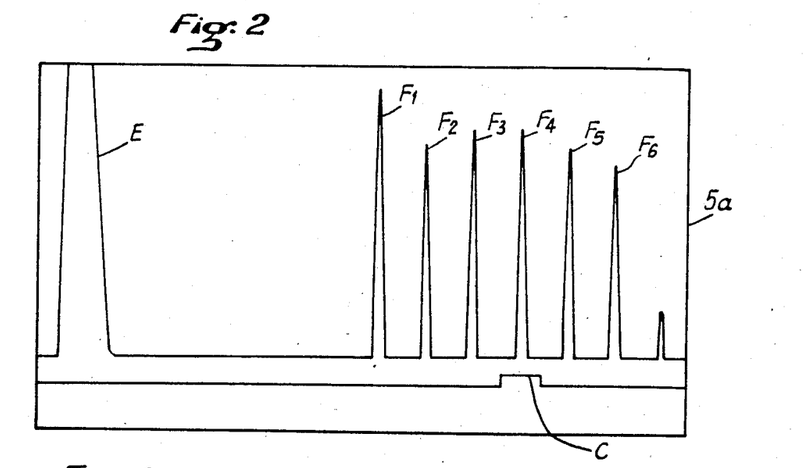
FIG. 2 is an A-scope representation.

FIG. 2 shows an A-scope representation such as appears on the oscilloscope of the device 5.

On this A-scope representation, in which the amplitude of the signals is plotted on the ordinates and the time on the abscissae, there is seen at E the injected pulse and at F1, F2, F3, F4, F5, F6 . . . a series of echoes. F1 is the direct main echo obtained by the reflection of the ultrasound in longitudinal waves (L in FIG. 3) from the end face of the bar opposite the injection end face after a single to and fro passage.

The spikes F2, F3, F4, F5, F6 . . . are secondary echoes which reach the transducer via the injection end face 3a of the bar via olbique paths and after various reflections from the lateral wall of the bar. There are produced inside the bar secondary wave beams in which waves of different types, longitudinal waves and transverse waves, are mixed together; transverse waves have a propagation speed which is lower than that of longitudinal waves.

Figure 3:
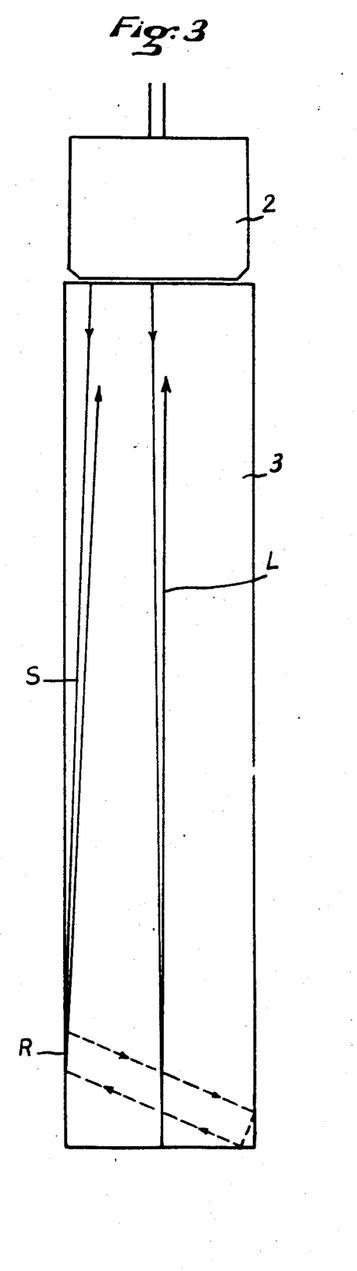

FIG. 3 shows a direct path of the longitudinal waves L and a path of a secondary wave S which produces the echo marked F3 in FIG. 2. The part of the path S shown in dashed line corresponds to transverse waves after reflection at the lateral surface and conversion into longitudinal waves at point R.

Figure 4A:
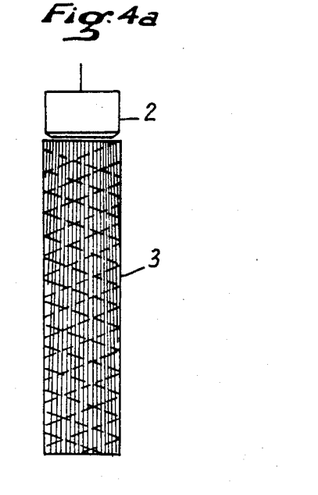

FIG. 4a represents schematically the beams reflected inside the bar 3 when the latter is immersed in a medium such as air. FIG. 4a' shows the display on the oscilloscope 5a of the echoes a, b, c, d which result from the surfaces and end of the bar 3. Only the first four echoes a, b, c, d are shown here, comprising the direct echo a and the first three secondary echoes b, c, d.

Figure 4B:
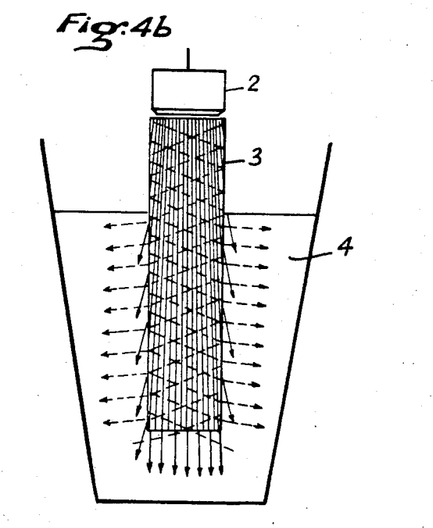

When the bar 3 is immersed in a different medium, containing a liquid or, more generally, a phase which brings about better transmission contact with the lateral surface of the bar 3, a fraction of the ultrasound escapes into the medium (FIG. 4b). There is seen in FIG. 4b' the reduction in the height of the echoes a, b, c, d. The secondary echoes b, c, d due overall to numerous successive reflections at the lateral surface of the bar 3 are very substantially affected by this modification. Measuring the height of one or more of the secondary echoes provides a means for monitoring the evolution with time of the medium or of an interface. It is advantageous to favor the formation of the secondary echoes by using a bar 3 which has a length/diameter ratio greater than 3.

Naturally, the lateral surface of the bar 3 must be as reflective as possible and it must retain its surface state while it is immersed in a changing medium. For this reason, a drawn glass bar is very suitable.

The formation of secondary echoes is thus favored by adhering to a certain relationship, as already mentioned, between the ultrasonic frequency and the thickness of the bar 3. The higher the frequency, the narrower the angle at the apex of the transmission cone and the thinner the bar must be in order for its lateral surface to be impinged on more frequently by the reflected waves. It is understood that here the term lateral surface relates to the entirety of the lateral surface of the bar over all the perimeter of its transverse cross-section, irrespective of its geometrical shape.

Figure 13:
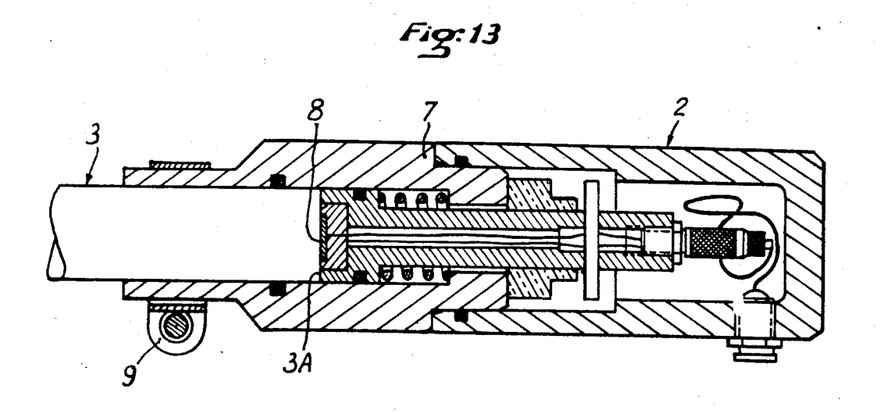
Figure 14:
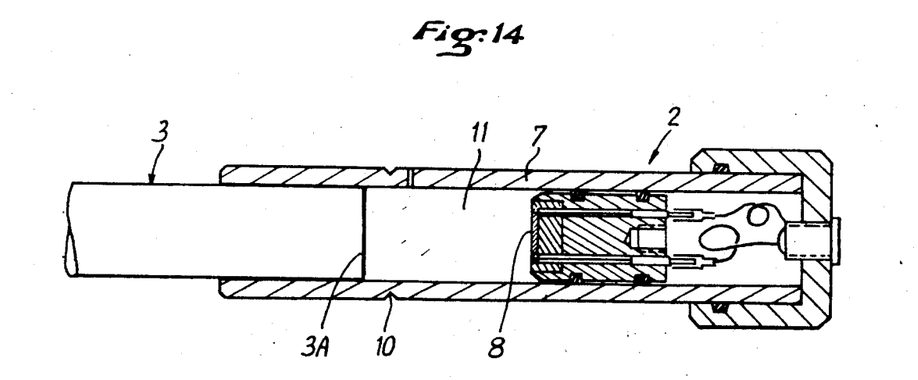

FIGS. 13 and 14 show a probe forming part of the apparatus of the invention comprising a head 2 from which extends an elongate bar 3 of smooth surfaced drawn glass; a probe of this kind is known as such and does not need to be described in detail. The head 2 comprises a body 7, preferably of two hollow parts fastened together, closed at one end and open at the opposite end to receive an end part of the bar 3 terminated by an end surface 3a perpendicular to its longitudinal direction. Within the body 7 there is disposed a transmitter-receiver ceramic 8, of known piezo or ferroelectric type, based on barium titanate, for example. In FIG. 3, the ceramic 8 is coupled to the bar 3 by direct contact with the end surface 3a of the latter; the end of the body 7 which receives the end part of the bar 3 is split longitudinally and clamped onto the bar 3 by means of a clip 9. In FIG. 14 the bar 3 is force-fitted into the body 7 but the latter features on its external surface, rearwardly of the end surface 3a of the bar 3, a circular groove 10 to facilitate breakage. The coupling between the ceramic 8 and the end surface 3a is effected through the intermediary of a liquid 11. In both cases the bar 3 is demountable from the head and it may be left behind in a medium which has been examined, for example in concrete the setting of which has been monitored.

As has been said hereinabove, when the bar 3 is placed in contact through its smooth lateral surface with a changing medium in which physico-chemical or biological changes are occurring, resulting in a corresponding variation in the fraction of the non-longitudinal waves which escape from the bar, these changes may be monitored and measured by observing the amplitude of the secondary echoes.

To obtain greater sensitivity for the apparatus it is preferable for the bar 3 to be immersed in the medium being monitored to virtually all of its length but, in certain circumstances, it is sufficient for its lateral surface to be brought appropriately into contact with the medium being monitored.

Reference will now be made to FIGS. 5 through 11 to provide actual examples of the application of the process of the invention.

In these figures the curves represent the evolution as a function of time (plotted in seconds along the abscissae) of the amplitude (plotted in volts along the ordinates) of a selected secondary echo recorded by means of the devices 5, 6 of FIG. 1 which may respectively be an apparatus such as that shown under the trade name "Ultrasonic type R7" or "Automatization type SM80" and a plotter known under the trade name "Sefram type Tyy". It should be noted that for most materials one part of the curve, which corresponds to the change of state, obtained by the process of the invention, is similar to a third degree curve. There is a correlation between the change of state of the medium (liquid—solid) or of the interface (non-oxidized—oxidized) and the point of inflection in this curve, which may be determined graphically or by calculation.

Figure 5:
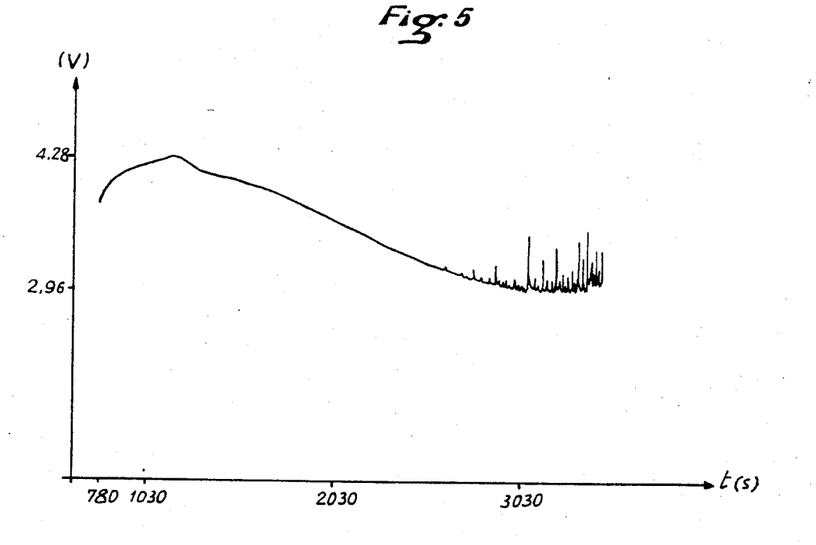

FIG. 5, which is a plot of the amplitude of the first secondary echo (b in FIG. 4b'), shows the changes on setting in a material known by the trade name "Plaster of Paris", characterized by a proportion of plaster to water of 1.5 by weight; the point of inflection is noted after a duration of 35.5 minutes. For this and the following tests, the glass bar 3 had a diameter of 20 mm and a length of 100 mm; the generator/transducer combination produced ultrasound at a frequency of 15 MHz.

Figure 6:
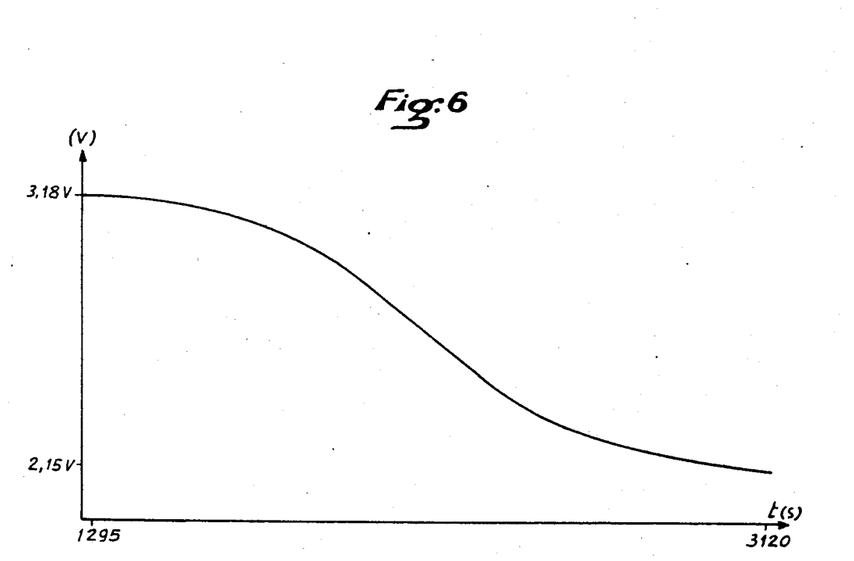

FIG. 6 shows the trend for the hardening of a known material consisting of a mixture of fine powder and a polymerizable resin under the influence of a hardener, marketed under the trade name "Metolux", having a unity ratio of hardener to resin. The point of inflection is located at approximately 37 minutes (2 220 s), determined graphically.

Figure 7:
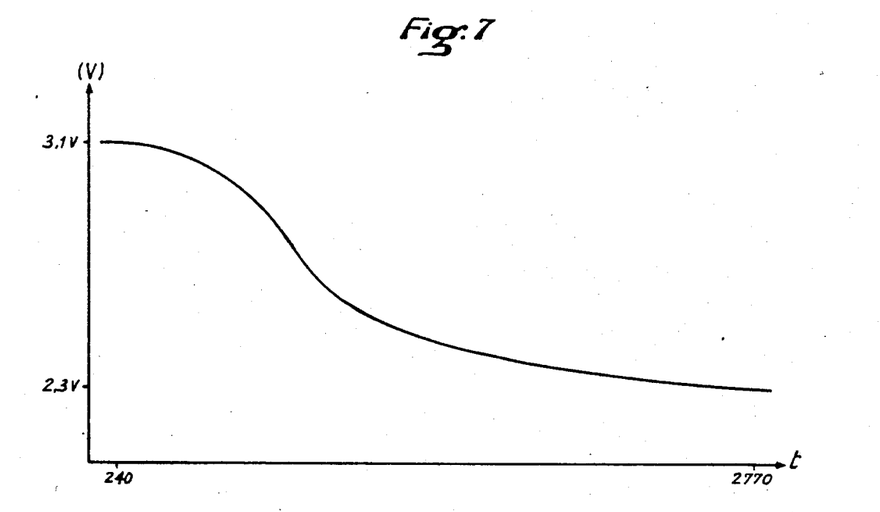

FIG. 7 shows the trend for the hardening of a material known under the trade name "Araldite Rapid" characterized by a ratio of hardener to epoxy resin of 0.6 by weight. The point of inflection is situated at approximately 14.6 minutes (determined graphically).

Figure 8:
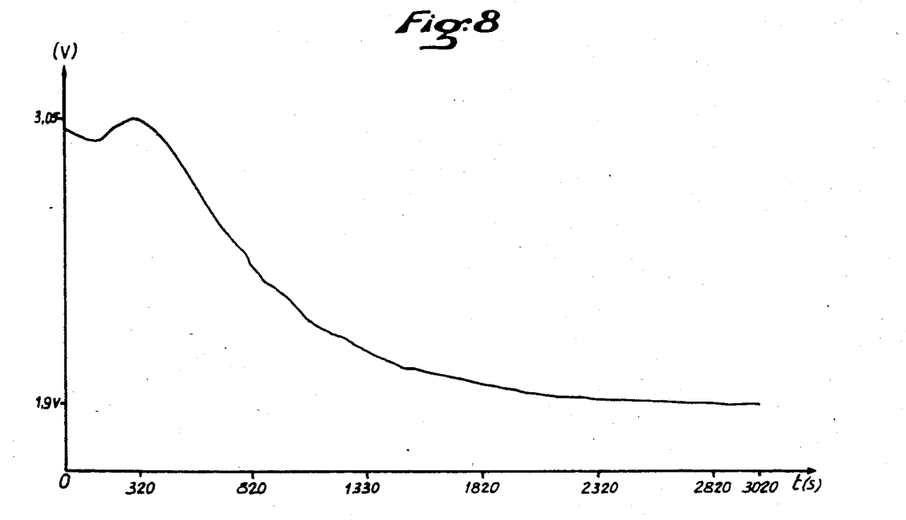

FIG. 8 shows the trend for the drying of a water-based paint. After an initial period which lasts approximately 400 s, the curve is approximately exponential. Its period (360 s) has been determined graphically.

Figure 9:
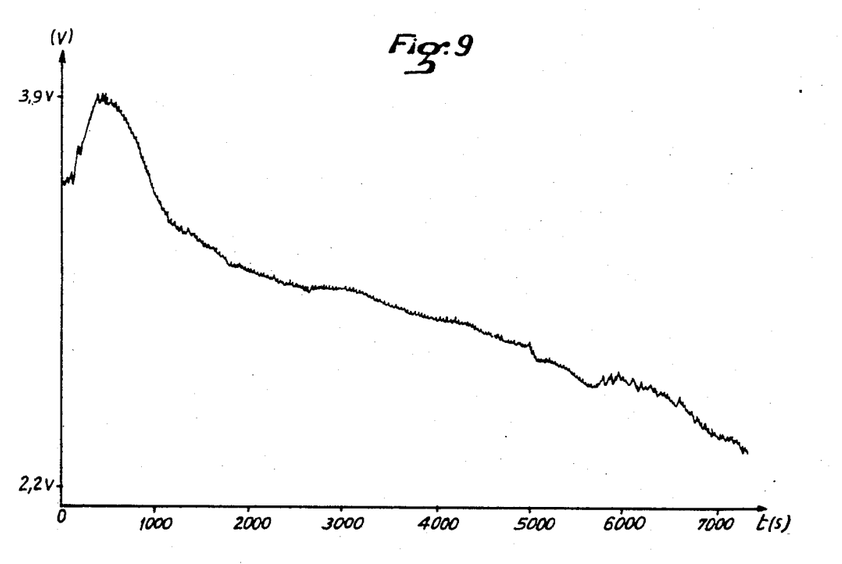

FIG. 9 shows the behavior of milk during curdling with the addition of 2 g of rennet per liter. In this case the measurement was taken on the second secondary echo (c in FIG. 4b').

Figure 10:
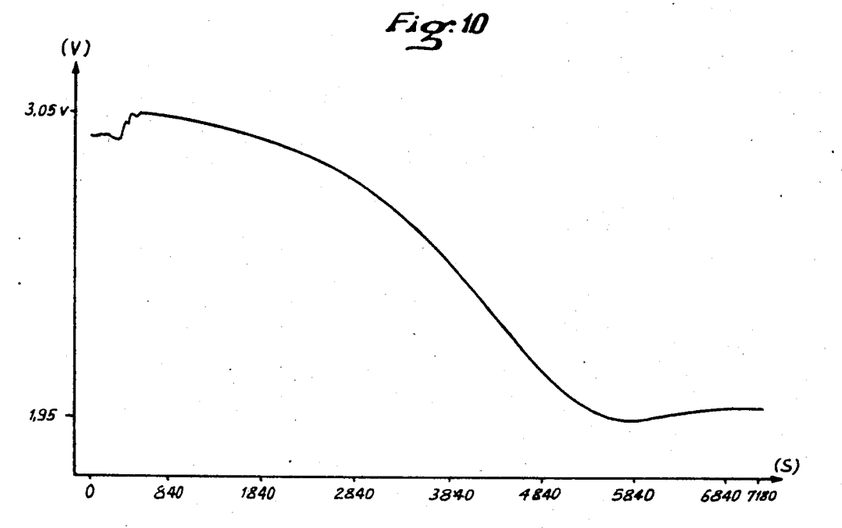

FIG. 10 shows the evolution of the corrosion of a bar with a diameter of 20 mm and a length of 100 mm of an aluminum alloy known under the trade name "Dural", immersed in a 41 g/liter solution of soda. The measurement was made by monitoring the evolution of the first secondary echo b.

Figure 11:
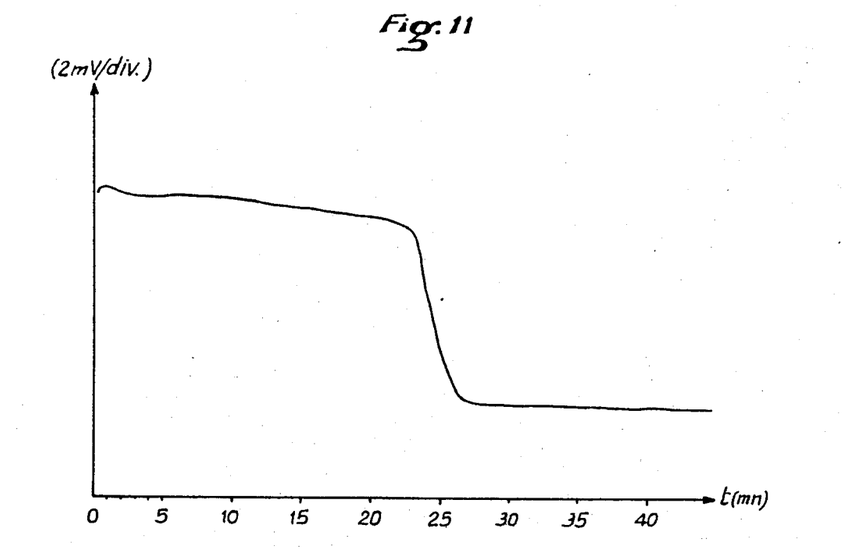

FIG. 11 shows the behavior of a polymerizable resin known under the trade name "Mecaprex" during polymerization. The measurement was made by recording the first secondary echo. On this figure the time is indicated in minutes and the voltage to a scale of 2 mV/division. The point of inflection is located at 24 minutes (determined graphically).

Figure 12:
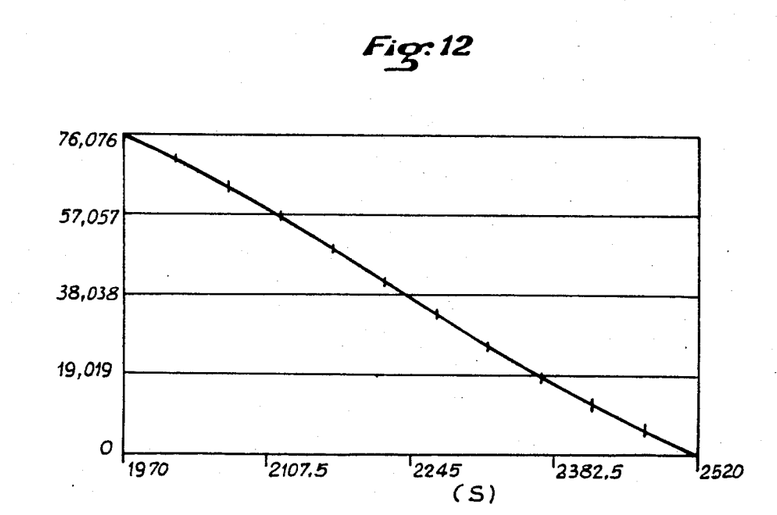
FIG. 12 shows an example of the determination by calculation of the point of inflection characterizing the change of state of a medium in the graph of FIG. 6, FIGS. 13 and 14 are respectively views in cross-section on a longitudinal plane of a probe for the apparatus of FIG. 1 with a bar which is detachable by demounting or by breaking off.

FIG. 12 shows an example of the mathematical determination of the point of inflection characterizing evolution of the hardening of the same product as in the example of FIG. 6. The calculation was carried out by obtaining the best fit to a third degree polynomial function using the least squares method. The abscissa of the point of inflection is 2 223 s and the slope at this point is $-0.154$.

It is clear that the process of the invention is in no way limited to the examples of the embodiments described and represented which have been given by way of example only. Moreover, the invention also covers all means constituting technical equivalents of the means described, as well as combinations thereof, and not exceeding its principle or its scope.

We claim:

1. A method of monitoring and measuring the changes with time of a physical or chemical characteristic within a medium or between two media by sensing diffusion in said medium or media of ultrasonic waves into a probe contacting said medium or media, comprising the steps of:
    generating in said probe longitudinal ultrasonic waves (L) propagating along a multiply-reflected path with an angle of incidence in said probe at the interface between said medium or media of said probe resulting in a mode conversion with longitudinal ultrasonic waves (L) and shear ultrasonic waves (S) generating numerous secondary echoes,
    detecting and collecting said secondary echoes through a collecting face of said probe by using a transducer,
    selecting one of said secondary echoes and observing a characteristic such as amplitude of said selected secondary echo for monitoring or measuring the evolution with time of said medium or media.

2. A method according to claim 1 wherein for said generating step and said collecting step the injection face and the collecting face are each an end face of the probe.

3. A method according to claim 2 wherein for said generating step and said collecting step the injection face and the collecting face are a same end face of the probe and said generating step includes selecting the ultrasonic frequency as a function of the thickness of said probe.

4. A method according to claim 1 wherein said detecting step includes immersing a substantial proportion of the length of said lateral surface into said medium or media.

5. Ultrasonic apparatus for monitoring and measuring the changes with time of a physical or chemical characteristic within a medium or between two media by sensing diffusion in said medium or media of ultrasonic waves generated into a probe having a lateral surface, comprising an ultrasonic transmitter coupled with an injection face of said probe for injecting by separate pulses longitudinal ultrasonic waves (L), generating by reflections on said lateral surface secondary beams of longitudinal waves (L) and shear waves (S), and secondary echoes into said probe, said probe having a smooth lateral surface for favoring numerous successive reflections on said smooth lateral surface of said injected ultrasonic waves, an ultrasonic receiver coupled with a collecting face of said probe for collecting at least some of said secondary beams reflected by said smooth lateral surface, following one of said separate pulses, a measuring device comprising electronic means coupled with said ultrasonic receiver for collecting as secondary echoes said reflected secondary beams, selecting one of said secondary echoes, measuring one characteristic of said selected secondary echo and recording the evolution with time of said characteristic.

6. Ultrasonic apparatus according to claim 5 wherein said probe is an elongate bar having at least one end surface and one lateral surface with a transversal thickness, said ultrasonic transmitter and said ultrasonic receiver being coupled with the said one end surface, said ultrasonic waves being selected between 1 MHz and 20 MHz, and said thickness of the bar being selected correspondingly in the respective range of 30 mm to 8 mm.

7. Ultrasonic apparatus according to claim 6 wherein said lateral surface has a length which is at least three times the transversal thickness of said elongate bar.

8. Ultrasonic apparatus according to claim 5 wherein said probe is of a material having a ratio of the propagation speeds of the longitudinal and transverse waves of between 1.57 and 1.70, and preferably of approximately 1.65.

9. Ultrasonic apparatus according to claim 5 wherein said probe is of drawn glass.

10. Ultrasonic apparatus according to claim 5 or claim 6 wherein said injection face and said collecting face are substantially perpendicular to the longitudinal dimension of said probe.

11. Ultrasonic apparatus according to claim 6 wherein said elongate bar has two end surfaces opposite one another, both being substantially perpendicular to the longitudinal dimension of said elongate bar, one of said end surfaces being used simultaneously as said injection face and said collecting face.

12. Ultrasonic apparatus according to claim 5 or claim 6 wherein said ultrasonic transmitter and said ultrasonic receiver comprise a head and said probe is connected with said head by detachable means.

* * * * *